US012624000B2

(12) United States Patent
Ma et al.

(10) Patent No.: US 12,624,000 B2
(45) Date of Patent: May 12, 2026

(54) PROCESS FOR SULFONATION OF 2-AMINOETHANOL HYDROGEN SULFATE ESTER TO PRODUCE TAURINE

(71) Applicant: Archer Daniels Midland Company, Decatur, IL (US)

(72) Inventors: Chi Cheng Ma, Champaign, IL (US); James Brazdil, Leland, NC (US); Hao Luo, Decatur, IL (US)

(73) Assignee: ARCHER-DANIELS-MIDLAND COMPANY, Decatur, IL (US)

( * ) Notice: Subject to any disclaimer, the term of this patent is extended or adjusted under 35 U.S.C. 154(b) by 643 days.

(21) Appl. No.: 18/000,801

(22) PCT Filed: Jun. 4, 2021

(86) PCT No.: PCT/US2021/036018
§ 371 (c)(1),
(2) Date: Dec. 5, 2022

(87) PCT Pub. No.: WO2021/248077
PCT Pub. Date: Dec. 9, 2021

(65) Prior Publication Data
US 2023/0227403 A1 Jul. 20, 2023

Related U.S. Application Data

(60) Provisional application No. 63/035,598, filed on Jun. 5, 2020.

(51) Int. Cl.
*C07C 303/24* (2006.01)
*B01D 9/00* (2006.01)

(52) U.S. Cl.
CPC .......... *C07C 303/24* (2013.01); *B01D 9/0013* (2013.01)

(58) Field of Classification Search
CPC ................................................... C07C 303/24
USPC ........................................................... 558/39
See application file for complete search history.

(56) References Cited

U.S. PATENT DOCUMENTS

| | | | |
|---|---|---|---|
| 4,657,704 | A | 4/1987 | Yamamoto et al. |
| 2005/0261370 | A1 | 11/2005 | Kimura et al. |
| 2015/0183731 | A1 | 7/2015 | Hu |
| 2015/0210905 | A1 | 7/2015 | Kaisha |

*Primary Examiner* — Taofiq A Solola
(74) *Attorney, Agent, or Firm* — Andrew F. Nilles

(57) ABSTRACT

A process comprises continuously adding a first stream and a second stream to a sulfonation vessel, wherein the first stream comprises aminoethanol sulfate ester (AES) and the second stream comprises an aqueous solution of sodium sulfite ($Na_2SO_3$). The process comprises continuously mixing the AES and the aqueous solution of $Na_2SO_3$ in the sulfonation vessel, thus producing a mixture. The process comprises continuously subjecting the mixture to heat in the presence of an inert gas, thus converting the AES to the taurine via sulfonation. In an aspect, the AES has a residence time of no more than four hours in the sulfonation vessel. In an aspect the heating step is conducted at a temperature of at least 115° C. and a pressure of at least 200 psi.

19 Claims, 3 Drawing Sheets

PROCESS FOR SULFONATION OF 2-AMINOETHANOL HYDROGEN SULFATE ESTER TO PRODUCE TAURINE

CROSS-REFERENCE TO RELATED APPLICATIONS

This application is a national stage entry of International Application No. PCT/US21/036018, filed Jun. 4, 2021, which itself claims priority to U.S. Provisional Patent Application No. 63/035,598, filed Jun. 5, 2020, each of the contents of the entirety of which are incorporated by this reference.

FIELD OF INVENTION

This invention relates to a continuous process for producing taurine from aminoethanol sulfate ester, also called 2-aminoethyl hydrogen sulfate ester (AES).

BACKGROUND OF THE INVENTION

Taurine, also known as 2-aminoethanesulfonic acid, is an amino acid that is found in natural dietary sources, biosynthesized in the body and is also produced by chemical synthesis for commercial purposes. Taurine is sometimes referred to as a conditional amino acid because it is derived from cysteine like other amino acids but lacks a carboxyl group that usually belongs to amino acids. Instead, it contains a sulfide group and can be called an amino sulfonic acid.

The world's annual consumption of taurine has been more than 50,000 tons, of which more than 80% are used as food and nutrition additives. Two methods have been used commercially to produce taurine, one method having ethylene oxide (EO) as starting material, and the other method having monoethanolamine (MEA) as starting material.

In the EO method, EO is reacted with sodium bisulfite to produce sodium isethionate, which is then converted via ammonolysis to sodium taurinate. Sodium taurinate is then neutralized to produce taurine. When sodium taurinate is neutralized with sulfuric acid, then a mixture of taurine and sodium sulfate is obtained. As disclosed in U.S. Pat. No. 8,609,890, sodium taurinate may be neutralized with sulfur dioxide to obtain taurine and to regenerate sodium bisulfite.

As disclosed in U.S. Pat. No. 9,145,359, one disadvantage of the EO method lies in the problematic quality of the product. More specifically, taurine produced via the EO method is a powder, and tends to form a hard cake over a short period of time during storage (in a matter of weeks), possibly due to the presence of unknown impurities. The process also involves some serious hazards from the viewpoint of safety since it uses ethylene oxide as a raw material, and ethylene oxide has extremely strong toxicity and carcinogenicity as well as posing considerable safety risks in its transport and handling. Moreover, the reaction from EO is carried out at very high temperatures (220-280° C.) and pressures (>100 bars).

In a conventional method using MEA as the starting material, taurine can be prepared by reacting MEA with sulfuric acid to obtain the intermediate 2-aminoethyl hydrogen sulfate ester (AES) and then sulfonating this ester intermediate. The MEA method uses a much safer starting material and produces a needle-shaped crystalline taurine product with excellent stability during transportation and storage as compared to the taurine powder produced in the EO method. A further advantage is the mild processing conditions as compared to the high temperature and pressures as required in the EO method.

A disadvantage of the MEA method on the other hand has been its higher cost of manufacture and higher capital expenditures, as compared to the EO method.

A further disadvantage of the MEA method is the lengthy time required for the sulfonation stage, typically from 35-40 hours, due to the slow reaction of AES and sodium sulfite. The MEA method also typically has a low product yield in the sulfonation step.

U.S. Pat. No. 9,145,359 discloses a method for the production of taurine by a cyclic process of reacting monoethanolamine, sulfuric acid, and ammonium sulfite in the presence of additives to inhibit the hydrolysis of 2-aminoethyl hydrogen sulfate ester (AES) intermediate. The patent states that the hydrolysis of AES is accelerated under both acidic and basic conditions, and contends that the yield of taurine can be drastically increased by strictly maintaining the pH of the reaction mixture from 6.0 to 8.0 and carrying out the sulfonation reaction at a temperature of 80 to 150° C. The patent discloses examples wherein starting materials were reacted in an autoclave equipped with a stirrer for 24 hours at 110° C. under autogenous pressure for 24 hours, and examples wherein starting materials were reacted in the same autoclave for 18 hours at 120° C.

U.S. Pat. No. 10,131,621 has the same named inventor as U.S. Pat. No. 9,145,359. U.S. Pat. No. 10,131,621 discloses an extraction process for recovering aminoalcohols and glycols from aqueous streams of taurine production. The aqueous streams which contain aminoalcohols and/or glycols are first mixed with a base to increase pH and then extracted with $C_3$-$C_6$ alcohols, ketones, and ethers. The aqueous streams are then returned to their respective cyclic process for the production of taurine. The patent states that according to the MEA process disclosed in U.S. Pat. No. 9,145,359, (i) monoethanolamine is reacted first with sulfuric acid to afford 2-aminoethyl hydrogen sulfate ester, which undergoes a sulfonation reaction with ammonium sulfite to yield a mixture of taurine and ammonium sulfate, and (ii) during the sulfonation reaction, up to 15% of the intermediate ester is hydrolyzed to monoethanolamine, which is left in the waste stream as its sulfate salt, along with ammonium sulfite and ammonium sulfate, or along with sodium sulfite and sodium sulfate when sodium sulfite is used as sulfonation agent.

Typical EO and MEA methods are both batch type processes that do not allow for continuous production of taurine.

It would be beneficial to have processes and products that do not have the disadvantages of these conventional methods. For example, it would be beneficial to have a continuous process that produces a stable crystalline taurine product. It would further be beneficial to have a continuous process that that produces stable crystalline taurine in a shorter period of time than the batch sulfonation stage of conventional MEA methods.

BRIEF SUMMARY OF THE INVENTION

The present invention provides advantages over conventional methods and products.

In a first aspect, the present invention relates to a process for continuously forming 2-aminoethanol hydrogen sulfate ester in a first, esterification step, by continuously reacting monoethanolamine with sulfuric acid with at least some concurrent water removal. This concurrent water removal in certain embodiments will be at least in part accomplished by contact with an inert particulate material during the esterification step which possesses the capability of receiving and removing water from the process as it is formed, then in these embodiments removing the inert particulate material to provide a 2-aminoethanol hydrogen sulfate ester product.

In certain other embodiments according to this first aspect, the concurrent water removal is accomplished at least in part by introduction of a feed comprising at least some monoethanolamine and at least some sulfuric acid into a spray dryer or thin film evaporator, and reacting the at least some monoethanolamine and the at least some sulfuric acid while using spray drying or thin film evaporation to remove water from the process.

In still other embodiments according to this first aspect, the concurrent water removal is accomplished at least in part by use of the inert particulate material with also carrying out some of the esterification within a spray dryer or thin film evaporator, In certain of these "combined water removal mode" embodiments, the spray drying or thin film evaporation follows some reaction of monoethanolamine with sulfuric acid in the presence of the inert particulate material to form 2-aminoethanol hydrogen sulfate ester, while in other embodiments the reaction of monoethanolamine with sulfuric acid in the presence of the inert particulate material is carried out substantially in the spray dryer or thin film evaporator. In a further aspect, the 2-aminoethanol hydrogen sulfate ester product from any of these embodiments can then be continuously sulfonated to produce taurine.

Preferably, the water removal accomplished in the first, esterification step by any means or combination of means will be sufficient to enable full conversion to the desired 2-aminoethanol hydrogen sulfate ester intermediate.

The present invention in another aspect relates to a process for continuously receiving and sulfonating a 2-aminoethanol hydrogen sulfate ester feed, such as but not being limited to a 2-aminoethanol hydrogen sulfate ester feed generated according to the present invention in its first aspect, which comprises continuously reacting a 2-aminoethanol hydrogen sulfate ester feed with sodium sulfite in an aqueous solution with heating in the presence of an inert gas in a sulfonation vessel, thereby converting the 2-aminoethanol hydrogen sulfate ester feed to taurine via sulfonation. In embodiments, the process further comprises subjecting the mixture to a pressure greater than autogenous pressure. In embodiments, the 2-aminoethanol hydrogen sulfate ester (AES) has a residence time in the sulfonation vessel of no more than four (4) hours. In embodiments, the 2-aminoethanol hydrogen sulfate ester (AES) has a residence time in the sulfonation vessel of no more than two (2) hours, the heat is a temperature of 140-155 degrees C., and the mixture is subjected to a pressure of at least 200 psi. Preferably in any of these embodiments, the process results in a taurine yield of at least 80%.

The present invention in yet another aspect relates to a process for continuously producing taurine by combining a process for continuously forming 2-aminoethanol hydrogen sulfate ester in a first, esterification step according to the present invention with a process for continuously receiving and sulfonating the 2-aminoethanol hydrogen sulfate ester from the first, esterification step to provide a taurine product. In embodiments, the taurine product is further refined.

These and other aspects, embodiments, and associated advantages will become apparent from the following Detailed Description.

DETAILED DESCRIPTION OF ILLUSTRATIVE EMBODIMENTS

Figure 1:
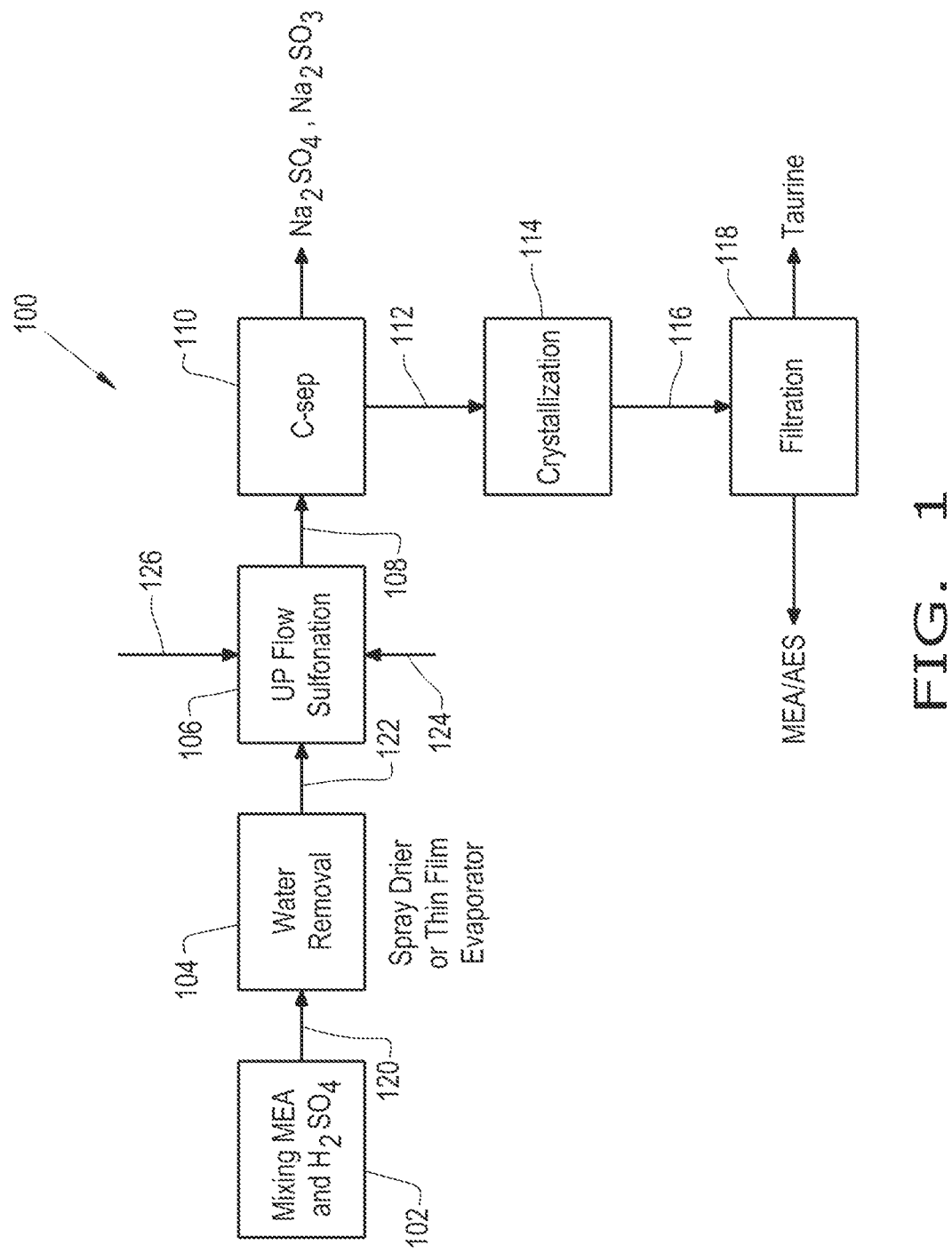
FIG. 1 is a process flow diagram of a continuous taurine production process in accordance with aspects of the invention.

FIG. 1 is a process flow diagram of an illustrative continuous taurine production process in accordance with aspects of the invention. As shown in FIG. 1, a continuous taurine manufacturing process 100 in one embodiment comprises a continuous first, esterification step 102 wherein monoethanolamine (MEA) and sulfuric acid (H$_2$SO$_4$) are continuously reacted, with at least some degree of concurrent water removal.

In certain embodiments as summarized above, this concurrent water removal involves use of an inert particulate material that possesses the capability of receiving and removing water from the esterification step as it progresses. In other embodiments, this concurrent water removal involves carrying out some of the esterification in the course of removing water from the process by spray drying or thin film evaporation. In still other embodiments, the water removal involves both use of an inert particulate material as well as spray drying or thin film evaporation.

In terms of the use of an inert particulate material with an intrinsic water removal capability, this capability can be associated, for example, with a porous inert particulate material wherein the pores are such as to receive and hold water as the esterification reaction proceeds, or with a material which readily forms stable hydrates as the esterification reaction proceeds. The inert particulate material will also preferably be substantially insoluble in all of sulfuric acid, monoethanolamine and water under the conditions of both the esterification step and the subsequent sulfonation step, so that the material can be readily separated by from the desired taurine product following the sulfonation step. A particularly suitable inert particulate material having these qualities is (anhydrous) sodium sulfate, which forms a stable decahydrate under the conditions of the esterification step and which is beneficially readily separable from the taurine, as is already known in the art.

The continuous esterification step 102 may, in respect of certain embodiments of using such a material for water removal, be initiated in advance of the introduction of the inert particulate material (or in advance of the initiation of contact with the inert particulate material by MEA, sulfuric acid or both) and then continued in the presence of the inert particulate material and with the associated water removal provided by the material, or in other embodiments, the inert particulate material can be introduced as either or both of monoethanolamine and sulfuric acid are provided to the esterification step 102, for example, in the form of a slurry of sodium sulfate in MEA.

In the same fashion, it will be understood that a water removal step 104 whereby water is removed as the esterification step progresses can occur to a degree concurrent with the esterification step 102 as well as following substantial completion of the esterification reaction and the formation of the 2-aminoethanol hydrogen sulfate ester intermediate, or can occur substantially concurrently with the esterification step 102. Thus, where water removal step 104 is performed using a spray dryer or thin film evaporator in addition to the inert particulate material, in certain embodiments, the spray drying or thin film evaporation follows some reaction of monoethanolamine with sulfuric acid in the presence of the inert particulate material to form 2-aminoethanol hydrogen sulfate ester (in some upstream vessel as suggested by effluent 120 or even in the combining of monoethanolamine and sulfuric acid for spraying into a spray dryer via a nozzle which is amenable to the introduction of a liquid including an inert particulate solid), while in other embodiments the reaction of monoethanolamine with sulfuric acid in the presence of the inert particulate material will be carried out substantially in the spray dryer or thin film evaporator—in effect, carrying out esterification step 102 and water removal step 104 concurrently, and eliminating a separate effluent 120 from esterification step 102. An example of the latter group of embodiments would involve spraying in (in the context of a spray dryer) or otherwise supplying (in the context of a thin film evaporator) the MEA and sulfuric acid separately—in certain embodiments including the inert particulate material such as sodium sulfate with the MEA or sulfuric acid to form a slurry which is sprayed into the spray dryer or supplied to the thin film evaporator.

Those of skill in the art will appreciate from the foregoing that there will be a number of different embodiments that could be considered for accomplishing the reaction of monoethanolamine and sulfuric acid with at least some assistance in removing water from the process by means of an inert particulate material with water removing capabilities, in terms of when and how the inert particulate material is introduced, whether or not additional water removal measures are undertaken, by what manner (e.g., spray drying, thin film evaporation or by other means) and when in relation to the formation of the 2-aminoethanol hydrogen sulfate ester, and that these various embodiments will have different advantages and disadvantages relative to one another. Ideally, however, the inert particulate material in combination with any other water removal device or means removes enough water to enable full conversion to the desired 2-aminoethanol hydrogen sulfate ester intermediate in the form of effluent 122, provide an AES intermediate that is free-flowing and not prone to fouling the walls of a spray dryer or downstream equipment leading to the sulfonation step as well as beneficially reduce water removal loads in the refining and purification of the finished taurine product, following the sulfonation step.

After water removal step 104, effluent 122 comprising AES is then sent to a sulfonation step 106. Sulfonation step 106 comprises continuously reacting AES with sodium sulfite ($Na_2SO_3$) to form taurine. During sulfonation step 106, sodium sulfate ($Na_2SO_4$) may also be formed, which as mentioned previously can be recycled (typically in part compared to the overall amount of sodium sulfate formed) to the esterification step 102 for use as an inert particulate material having water removal capabilities. Sulfonation step 106 may comprise using an upflow or downflow sulfonation reactor wherein effluent 122 comprising AES is continuously pumped to the bottom or top of the sulfonation reactor. Similarly, a stream 124 comprising aqueous sodium sulfite is continuously pumped to the bottom or top of the sulfonation reactor. In the sulfonation reactor, AES is continuously mixed and reacts with sodium sulfite present in the sulfonation reactor. The sulfonation reactor may be sealed with a pressure head with an inert gas 126 (e.g., nitrogen gas). Sulfonation step 106 comprises continuously subjecting the mixture of AES and sodium sulfite to heat in the presence of the inert gas. The heat may be a predetermined reaction temperature. In an aspect, the mixture of AES and sodium sulfite is continuously subjected to a pressure greater than autogenous pressure. In an aspect, the pressure may be exerted through the use in the sulfonation reactor of at least 200 psi inert gas (e.g., $N_2$). In an aspect, the heat may be at least 115° C. In an embodiment, the heat may be at least 120° C. In a preferred embodiment, the heat may be 120-155° C. In a more preferred embodiment, the heat may be 140-155° C. Effluent 108 from sulfonation step 106 comprises taurine and may also comprise $Na_2SO_4$ and $Na_2SO_3$, as well as unreacted AES.

Effluent 108 from sulfonation step 106 may then in certain embodiments be processed to remove the sodium sulfate, by means and methods known in the art. The insolubility of sodium sulfate in water lends itself, in particular, to a recovery of the sodium sulfate by precipitation, but other means may be conceived and used by those familiar with the manufacture of taurine and with the properties of sodium sulfate. The water of hydration acquired by the sodium sulfate in the esterification step 102 is then removed with heating for at least a recycle portion of the sodium sulfate, and the preferably anhydrous sodium sulfate in the recycle portion is then recycled back to the esterification step 102.

Where sodium sulfate is used as an inert particulate material in the esterification step 102, then sodium sulfite is understandably preferably recovered separately from the sodium sulfate, for example, by a chromatography step 110.

Effluent 112 from chromatography step 110 comprises taurine, and in certain embodiments the effluent 112 may be conveyed to crystallization step 114 to recover the taurine. The crystallization step 114 may comprise cooling effluent 112 from an elevated temperature, e.g., about 100° C., to a lower temperature, e.g., about 28° C. Crystallization step 114 may be preceded by a water removal step (not shown in FIG. 1) wherein further water is removed from effluent 112, e.g., by distillation, thereby concentrating the amount of taurine in effluent 112 prior to crystallization.

Effluent 116 from crystallization step 114 comprises crystallized taurine and may be conveyed to filtration step 118. In filtration step 118, crystallized taurine is separated from any unreacted AES.

Alternatively, effluent 112 may in certain embodiments be conveyed directly to the filtration step 118, with additional water removal again optionally preceding a cooling of the effluent 112 to cause the taurine to precipitate as a filterable mass from any unreacted AES from the sulfonation step 106.

Figure 2:
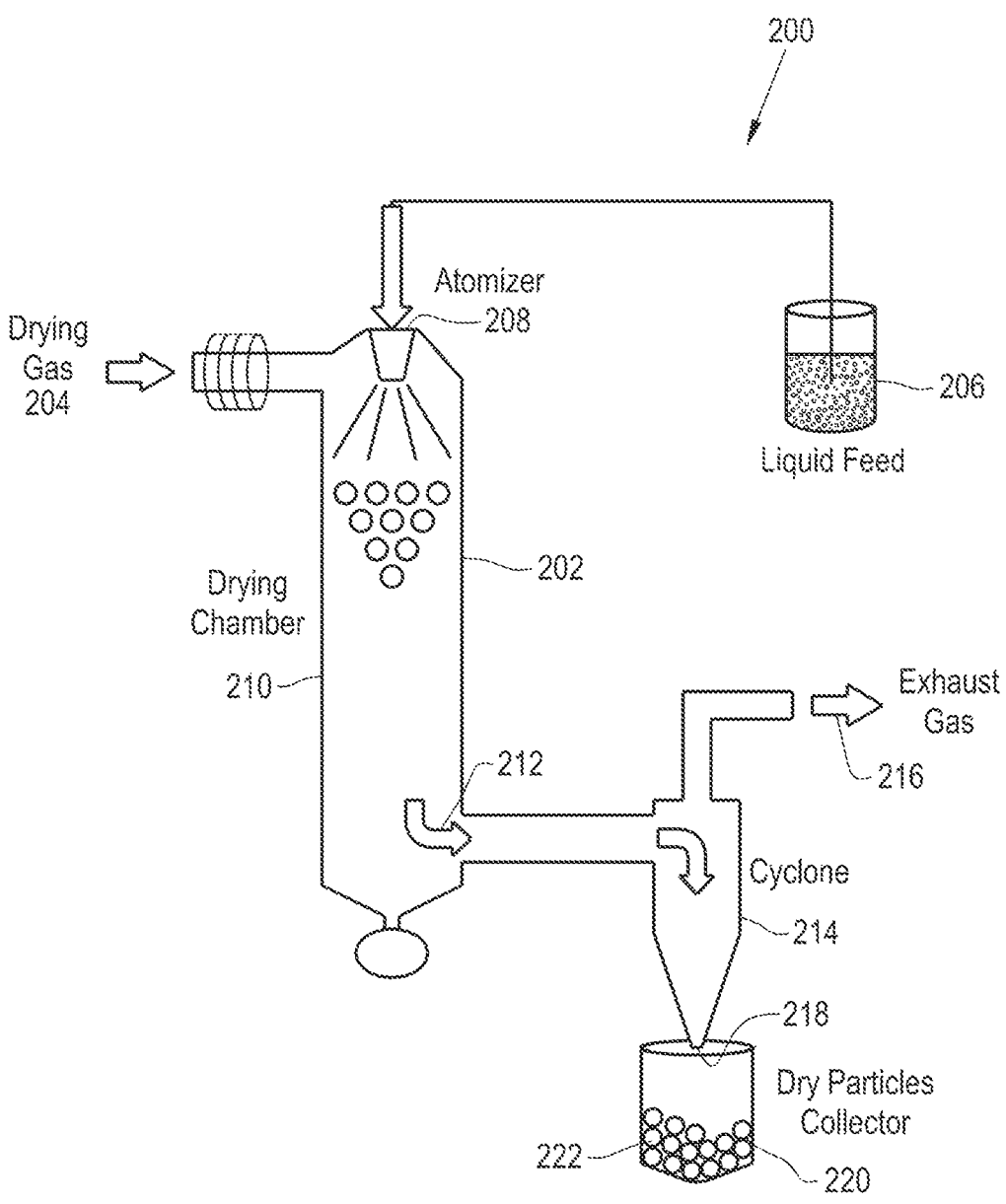
FIG. 2 depicts a drying apparatus for water removal in accordance with aspects of the invention.

FIG. 2 depicts a purely illustrative drying apparatus 200 for accomplishing an additional measure of water removal in accordance with aspects of the invention. Drying apparatus 200 comprises spray dryer 202. Drying apparatus 200 comprises drying gas 204. Drying gas 204 may be an inert gas, e.g., $N_2$. Liquid feed 206 may be the same as effluent 120 shown in FIG. 1, though as already mentioned, in other embodiments a mixture of substantially unreacted monoethanolamine and sulfuric acid can be supplied directly to the spray dryer 202 (in an embodiment, with inert particulate material such as sodium sulfate being included in one or the other or both in a slurry form) or MEA, sulfuric acid or both may be independently supplied to the spray dryer in any manner known to those in the spray drying art—in co-current or countercurrent flows.

Spray dryer 202 may comprise drying chamber 210 and an atomizer 208 configured to atomize a liquid feed 206. Effluent 212 from spray dryer 202 may be conveyed to cyclone 214. In cyclone 214, exhaust gas 216 is separated from effluent 222. Effluent 222 exits cyclone 214 through opening 218. Effluent 222, comprising unreacted AES, may be collected in a collector 220. Effluent 222 may be the same as effluent 122 shown in FIG. 1. Thus, effluent 222 comprising AES has less water than liquid fee 206.

Figure 3:
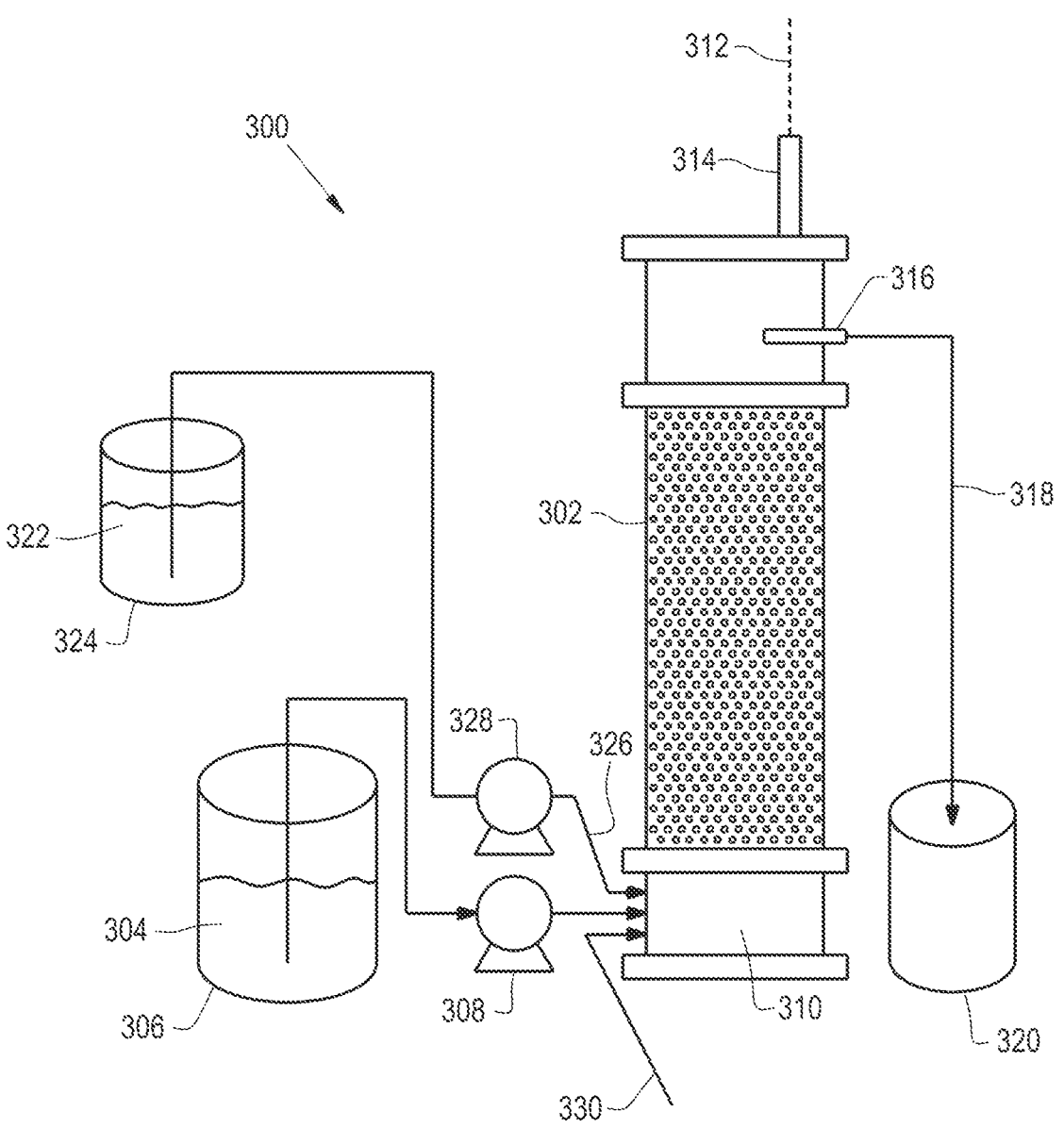
FIG. 3 depicts an apparatus for sulfonation in accordance with aspects of the invention.

FIG. 3 depicts apparatus 300 for sulfonation step 106 shown in FIG. 1 in accordance with aspects of the invention. As shown in FIG. 3, apparatus 300 may comprise an upflow sulfonation reactor 302. Those skilled the art having the benefit of the present disclosure will recognize that the sulfonation reactor may be a downflow sulfonation reactor. Feed 304 in feed vessel 306 may be degassed by an inert gas prior to being conveyed out of feed vessel 306. The inert gas may be any suitable inert gas, including but not limited to nitrogen, helium, argon, and combinations thereof. In a preferred embodiment, the inert gas is nitrogen. Feed 304 is continuously conveyed out of feed vessel 306 by pump 308 to bottom 310 of upflow sulfonation reactor 302. Feed 304 may be the same as effluent 222 shown in FIG. 2. Thus, feed 304 comprises AES. As shown in FIG. 3, AES may be continuously pumped to the bottom of the sulfonation reactor 302. In sulfonation reactor 302, AES reacts with sodium sulfite present in the sulfonation reactor 302 to form taurine.

Aqueous sodium sulfite 322 in vessel 324 may be degassed by an inert gas prior to being conveyed out of vessel 324. The inert gas may be any suitable inert gas, including but not limited to nitrogen, helium, argon, and combinations thereof. In a preferred embodiment, the inert gas is nitrogen. Aqueous sodium sulfite 322 is continuously conveyed out of vessel 324 as stream 326 by pump 328 to bottom 310 of upflow sulfonation reactor 302. Stream 326 comprising aqueous sodium sulfite 322 may be the same as stream 124 shown in FIG. 1. Sulfonation reactor 302 may be sealed with a pressure head with an inert gas, e.g., inert gas 330. Inert gas 330 may be the same as inert gas 126 shown in FIG. 1. Thus, sulfonation step 106 shown in FIG. 1 may be performed in apparatus 300 shown in FIG. 3. Sulfonation reactor 302 may be operated by heating the reaction mixture of AES and aqueous sodium sulfite at a reaction temperature and under a reaction pressure, e.g., a reaction pressure of at least 200 psi inert gas (e.g., $N_2$). The reaction temperature may be at least 115° C. In an embodiment, the reaction temperature may be at least 120° C. In a preferred embodiment, the reaction temperature may be 120-155° C. In a more preferred embodiment, the reaction temperature may be 150-155° C. Via conduit 316, effluent 318 may be collected in vessel 320. Effluent 318 may be the same as effluent 108 shown in FIG. 1. Thus, effluent 318 comprises taurine, and may also comprise $Na_2SO_4$ and $Na_2SO_3$, as well as unreacted AES. Exhaust gas 312 comprising inert gas may exit sulfonation reactor 302 through conduit 314 as may be desired, e.g., to purge materials in sulfonation reactor, or maintain a predetermined pressure in the sulfonation reactor 302.

In regard to a preferred sulfonation method as thus described, we have found that the conversion of aminoethanol hydrogen sulfate ester to taurine via sulfonation is dramatically improved by heating the mixture of sodium sulfite and aminoethanol hydrogen sulfate ester in the presence of an inert gas. In an aspect the heating step is conducted at a temperature of at least 115° C. and a pressure greater than autogenous pressure. In an aspect, the heating step is conducted at a pressure of at least 50 psi, more preferably at least 100 psi, and even more preferably at least 200 psi. In an aspect, the process results in a taurine yield of at least 80%. In an aspect, the process results in at least a 95% AES conversion to taurine. In an aspect, the aminoethanol hydrogen sulfate ester has a residence time of no more than four (4) hours in the sulfonation vessel. This residence time of no more than four (4) hours of the aminoethanol hydrogen sulfate ester in the reaction vessel during sulfonation conversion to taurine is a substantially less than the period of time for sulfonation in conventional MEA methods. In an aspect, the aminoethanol hydrogen sulfate ester has a residence time of no more than two (2) hours in the sulfonation vessel.

The following examples further describe taurine synthesis in accordance with aspects of the present invention.

Example 1

A 300 cc Hasteloy autoclave reactor was charged with 35 g of $Na_2SO_3$, 150 g water, and heated to 50° C. to dissolve $Na_2SO_3$. After dissolving $Na_2SO_3$ in the water, 28 g of aminoethanol sulfate ester (AES) solid was added to autoclave reactor. The autoclave reactor was then sealed with a pressure head, purged three time with $N_2$ gas, then heated to 115° C. for sixteen (16) hours with 244 psi $N_2$ gas. After this time, the reaction was quenched by flash cooling in an ice bath. Once the thermocouple temperature read 20° C., the pressure head was removed, and liquid transferred to a storage vessel. The product was analyzed by LC and $^1H$, C13 NMR. Results from these analyses indicated a 100% AES conversion with 85% taurine yield.

Example 2

A 300 cc Hasteloy autoclave reactor was charged with 35 g of $Na_2SO_3$, 150 g water, and heated to 50° C. to dissolve $Na_2SO_3$. After dissolving $Na_2SO_3$ in the water, 28 g of aminoethanol sulfate ester (AES) solid was added to autoclave reactor. The autoclave reactor was then sealed with a pressure head, purged three time with $N_2$ gas, then heated to 115° C. for five (5) hours with 900 psi $N_2$ gas. After this time, the reaction was quenched by flash cooling in an ice bath. Once the thermocouple temperature read 20° C., the pressure head was removed, and liquid transferred to a storage vessel. The product was analyzed by LC and $^1H$, C13 NMR. Results from these analyses indicated that an 86% AES conversion with 82% taurine yield.

Example 3

A 250 ml round bottom flask was charged with 18 g of $Na_2SO_3$, 75 g water, and heated to 50° C. to dissolve $Na_2SO_3$. After dissolving $Na_2SO_3$ in the water, 14 g of aminoethanol sulfate ester (AES) solid was added to flask. The flask was refluxed at 115° C. for thirty (30) hours. After this time, the reaction was quenched by flash cooling in an ice bath. The product was analyzed by LC and $^1H$, C13 NMR. Results from these analyses indicated a 73% AES conversion with 68% taurine yield.

Example 4

A 300 cc Hasteloy autoclave reactor was charged with 35 g of $Na_2SO_3$, 150 g water, and heated to 50° C. to dissolve $Na_2SO_3$. After dissolving $Na_2SO_3$ in the water, 28 g of aminoethanol sulfate ester (AES) solid was added to reactor. The reactor was then sealed with a pressure head, purged three time with $N_2$ gas, then heated to 105° C. for six (6) hours with 200 psi $N_2$ gas. After this time, the reaction was quenched by flash cooling in an ice bath. Once the thermocouple temperature read 20° C., the pressure head was removed, and liquid transferred to a storage vessel. The product was analyzed by LC and $^1H$, $^{13}C$ NMR. Results from these analyses indicated a 62% AES conversion with 58% taurine yield.

Example 5

A 300 cc Hasteloy autoclave reactor was charged with 35 g of $Na_2SO_3$, 150 g water, and heated to 50° C. to dissolve $Na_2SO_3$. After dissolving $Na_2SO_3$ in the water, 28 g of aminoethanol sulfate ester (AES) solid was added to reactor. The reactor was then sealed with a pressure head, purged three time with $N_2$ gas, then heated to 115° C. for five (5) hours with 900 psi $N_2$ gas. After this time, the reaction was quenched by flash cooling in an ice bath. Once the thermocouple temperature read 20° C., the pressure head was removed, and liquid transferred to a storage vessel. The product was analyzed by LC and $^1H$, $^{13}C$ NMR. Results from these analyses indicated an 86% AES conversion with 81% taurine yield.

The above examples indicated that elevated temperature under pressure with an inert gas, such as $N_2$ gas, improves taurine yield and reduces the sulfonation reaction time. Example 3 had a sulfonation stage with a reaction time of thirty (30) hours and was not under pressure with $N_2$ gas. Examples 1, 2, 4, and 5, had much shorter sulfonation stages of either five (5) or (six) hours under pressure with $N_2$ gas.

Example 6

The following example demonstrates a method wherein a thin film evaporator is used to remove water. The thin film evaporator may be used for the water removal step 104 shown in FIG. 1. In accordance with reacting step 102 shown in FIG. 1, MEA (20 g) was charged into a 250 ml flask equipped with a stirrer and a thermometer. $H_2SO_4$ (36 g) was slowly added into the flask over 30 minutes employing a dropping funnel. The reactor used for the water removal step was placed in an ice/water bath during the initial $H_2SO_4$ addition to control the exothermic acid-base reaction. The above mixture was transferred to addition funnel and slowly added to the thin film evaporator, wherein the thin film evaporator had a temperature of 150° C. and 30 torr vacuum. White solids were collected and analyzed using NMR, HPLC analysis, and the resulting analysis demonstrated 95% purity and 85% recovery yield

Example 7

The following example demonstrates a method wherein a spray dryer is used to remove water. The spray dryer may be used for the water removal step 104 shown in FIG. 1. In accordance with reacting step 102 shown in FIG. 1, In accordance with reacting step 102 shown in FIG. 1, MEA (12 g) was charged into a 250 ml flask equipped with a stirrer and a thermometer. $H_2SO_4$ (20 g) molar ratio (1:1) was slowly added into the flask over 30 minutes employing a dropping funnel.

The above mixture was transferred to a small bottle and slowly added to the spray dryer with the inlet and outlet temperatures indicated in Table 1 below, at a pumping rate at 3 mL/min and with a drying gas flow at 40 mm (473 L/hr). White solids were collected and analyzed using NMR, HPLC analysis, and the resulting analysis demonstrated 99% purity and 85.5% recovery yield as shown in Table 1 below.

TABLE 1

| Solid AES Recovery yield (wt %) | Purity (mol %) (Based on NMR) | Mass Balance mol % | Inlet temp. (° C.) | Outlet temp. (° C.) |
|---|---|---|---|---|
| 85.5 | 99.0 | 85.4 | 200 | 140 |

Example 8

Monoethanolamine (MEA) and sulfuric acid were premixed at a 1:1 molar ratio by slowly adding concentrated sulfuric acid into MEA in an ice bath. 3 wt % of anhydrous sodium sulfate was added to the premixed MEA and sulfuric acid mixture. This mixture was then fed into the same spray dryer used in Example 7 through a peristaltic pump and a spray nozzle for the generation of 2-aminoethyl hydrogen sulfate ester (AES). The inlet temperature of the spray dryer instrument was approximately 190 degrees Celsius. The drying gas was set at a gas flow rate of 470 L/h. The flow rate of the feed to the spray dryer was about 1.5 mL/min. The aspirator output of the instrument was set at 100% for all the experiments. After reaction, the generated 2-aminoethyl hydrogen sulfate (AES) was in the form of a more free-flowing, less tacky white solid as compared to that obtained in Example 7. The product was then collected and analyzed by 1H NMR and UPLC, and the addition of sodium sulfate was thereby confirmed as enabling improved yields of a comparable purity AES product to that obtained under the same circumstances but absent the addition of the anhydrous sodium sulfate.

Example 9

Monoethanolamine (MEA) and sulfuric acid were premixed at a 1:1 molar ratio by slowly adding concentrated sulfuric acid into the MEA in an ice bath. 3 wt % of anhydrous sodium sulfate was added to the premixed MEA and sulfuric acid mixture. This mixture was then fed into the spray dryer through a peristaltic pump and a spray nozzle for the generation of 2-aminoethyl hydrogen sulfate ester (AES). The inlet temperature of the spray dryer instrument was approximately 160 degrees Celsius. The drying gas was set at a gas flow rate of 470 L/h. The flow rate of the feed to the spray dryer was 1.5 mL/min. The aspirator output of the instrument was set at 100% for all the experiments. After reaction, the generated 2-aminoethyl hydrogen sulfate ester (AES) was again in the form of a more free flowing, less tacky white solid as compared to that obtained in Example 7. The product was then collected and analyzed by 1H NMR and UPLC, and the addition of sodium sulfate was thereby confirmed as enabling improved yields of a comparable purity AES product to that obtained under the same circumstances but absent the addition of the anhydrous sodium sulfate.

Example 10

In the same fashion as Examples 8 and 9, MEA and sulfuric acid were premixed at a 1:1 molar ratio by slowly adding concentrated sulfuric acid into MEA in an ice bath. 3 wt % of anhydrous sodium sulfate was again added to the premixed MEA and sulfuric acid mixture. This mixture was then fed into the spray dryer through a peristaltic pump and a spray nozzle for the generation of 2-aminoethyl hydrogen sulfate ester (AES). The inlet temperature of the spray dryer instrument was 170 degrees Celsius. The drying gas was supplied at 470 L/h. The feed was supplied to the spray nozzle at 1.5 mL/min. The aspirator output of the instrument was set at 100% for all the experiments. After reaction, the generated 2-aminoethyl hydrogen sulfate ester (AES) was in the form of a more free flowing, less tacky white solid as compared to that obtained in Example 7. The product was then collected and analyzed by 1H NMR and UPLC, and the addition of sodium sulfate was thereby confirmed as enabling improved yields of a comparable purity AES product to that obtained under the same circumstances but absent the addition of the anhydrous sodium sulfate,

Example 11

In the same fashion as Examples 8 and 9, MEA and sulfuric acid were premixed at a 1:1 molar ratio by slowly adding concentrated sulfuric acid into MEA in an ice bath. 3 wt % of anhydrous sodium sulfate was again added to the premixed MEA and sulfuric acid mixture. This mixture was then fed into the spray dryer through a peristaltic pump and a spray nozzle for the generation of 2-aminoethyl hydrogen sulfate ester (AES). The inlet temperature of the spray dryer instrument was 180 degrees Celsius. The drying gas was supplied at 470 L/h. The feed was supplied to the spray nozzle at 1.5 mL/min. The aspirator output of the instrument was set at 100% for all the experiments. After reaction, the generated 2-aminoethyl hydrogen sulfate ester (AES) was in the form of a more free flowing, less tacky white solid as compared to that obtained in Example 7. The product was then collected and analyzed by 1H NMR and UPLC, and the addition of sodium sulfate was thereby confirmed as enabling improved yields of a comparable purity AES product to that obtained under the same circumstances but absent the addition of the anhydrous sodium sulfate,

Example 12

In the same fashion as Examples 8 and 9, MEA and sulfuric acid were premixed at a 1:1 molar ratio by slowly adding concentrated sulfuric acid into MEA in an ice bath. 3 wt % of anhydrous sodium sulfate was again added to the premixed MEA and sulfuric acid mixture. This mixture was then fed into the spray dryer through a peristaltic pump and a spray nozzle for the generation of 2-aminoethyl hydrogen sulfate ester (AES). The inlet temperature of the spray dryer instrument was 200 degrees Celsius. The drying gas was supplied at 470 L/h. The feed was supplied to the spray nozzle at 1.5 mL/min. The aspirator output of the instrument was set at 100% for all the experiments. After reaction, the generated 2-aminoethyl hydrogen sulfate ester (AES) was in the form of a more free flowing, less tacky white solid as compared to that obtained in Example 7. The product was then collected and analyzed by 1H NMR and UPLC, and the addition of sodium sulfate was thereby confirmed as enabling improved yields of a comparable purity AES product to that obtained under the same circumstances but absent the addition of the anhydrous sodium sulfate,

Example 13

The following example demonstrates a method with up flow sulfonation.

30 cc reactors were built with stainless steel with bodies and an internal diameter (ID) of 0.61 inches. The reactors are jacketed and are heated with circulating oil. Reactor temperatures are monitored via an internal thermowell ⅛" with a 1/16" thermocouple that can slide up and down to monitor peak temperature. The temperature of the jacket is monitored by measuring the oil temperature just before it enters the jacket. The temperatures of the reactors are controlled by adjusting the oil temperature. The inlets of the reactors are attached to an Isco dual piston pump and mass flow controllers for supplying gases. The outlet was attached to a condenser kept at 5° C. by a chiller unit. The pressures of the reactors are controlled using a dome loaded back pressure regulator (Mity Mite brand).

Experimental Conditions: Jacket Temperature=140° C.; Liquid Hourly Space Velocity (LHSV)=0.5 (i.e., two (2) hours); $N_2$ Flow=100 ml/min; up flow AES Concentration=10.6% by wt.; Sulfite/AES molar ratio=1.9; pH=6.8.

Products of the reaction were analyzed by HPLC. These analyses indicated 100% AES conversion with taurine yield at 83%.

Those having skill in the art, with the knowledge gained from the present disclosure, will recognize that various changes can be made to the disclosed processes in attaining these and other advantages, without departing from the scope of the present disclosure. As such, it should be understood that the features of the disclosure are susceptible to modifications and/or substitutions. The specific embodiments illustrated and described herein are for illustrative purposes only, and not limiting of the invention as set forth in the appended claims.

What is claimed is:

1. A process for continuously forming 2-aminoethanol hydrogen sulfate ester, comprising:
   continuously reacting monoethanolamine with sulfuric acid with at least some concurrent water removal, to provide an 2-aminoethanol hydrogen sulfate ester product;
   wherein the concurrent water removal is accomplished by contacting an inert particulate material with the monoethanolamine and the sulfuric acid;
   wherein the inert particulate material possesses the capability of receiving and removing water from the process.

2. The process of claim 1, further comprising removing the inert particulate material including its associated water from the process.

3. The process of claim 1, wherein the concurrent water removal further comprises removing water from the process by spray drying or thin film evaporation.

4. The process of claim 3, wherein the spray drying, or thin film evaporation follows some reaction of monoethanolamine with sulfuric acid in the presence of the inert particulate material to form 2-aminoethanol hydrogen sulfate ester.

5. The process of claim 3, wherein the reaction of monoethanolamine with sulfuric acid in the presence of the inert particulate material is carried out substantially in the spray dryer or thin film evaporator and water is concurrently removed by means both of the inert particulate material and the spray drying or thin film evaporation.

6. A process for continuously producing taurine, comprising continuously forming 2-aminoethanol hydrogen sulfate ester by the process of claim 5 and continuously sulfonating the 2-aminoethanol hydrogen sulfate ester so produced to provide taurine.

7. A process for continuously producing taurine, comprising:
   a) continuously adding a first stream and a second stream to a sulfonation vessel, wherein the first stream comprises an aminoethanol hydrogen sulfate ester (AES) feed and the second stream comprises an aqueous solution of sodium sulfite ($Na_2SO_3$);
   b) continuously mixing the aminoethanol hydrogen sulfate ester (AES) feed and the aqueous solution of sodium sulfite ($Na_2SO_3$) in the sulfonation vessel, thus producing a mixture; and c) continuously subjecting the mixture to heat in the presence of an inert gas, thus converting aminoethanol hydrogen sulfate ester (AES) in the feed to provide a crude taurine product via sulfonation.

8. The process of claim 7, wherein the aminoethanol hydrogen sulfate ester (AES) has a residence time of no more than four hours in the sulfonation vessel.

9. The process of claim 7, wherein the inert gas is selected from the group consisting of nitrogen, argon, helium, and combinations thereof.

10. The process of claim 7, further comprising subjecting the mixture to a pressure greater than autogenous pressure.

11. The process of claim 7, wherein the presence of the inert gas subjects the mixture to the pressure greater than autogenous pressure.

12. The process of claim 7, further comprising subjecting the mixture to a pressure to at least 50 psi.

13. The process of claim 7, wherein the heat is a temperature of at least 115° C.

14. The process of claim 7, wherein the aminoethanol hydrogen sulfate ester feed is continuously generated upstream of the sulfonation vessel.

15. The process of claim 14, further comprising separating $Na_2SO_4$ and $Na_2SO_3$ from the crude taurine product to provide a refined taurine product.

16. The process of claim 15, wherein the separating of $Na_2SO_4$ and $Na_2SO_3$ from the crude taurine product is performed at least in part by chromatography.

17. The process of claim 15, wherein the separating of $Na_2SO_4$ and $Na_2SO_3$ from the crude taurine product is performed at least in part by crystallization.

18. The process of claim 7, wherein the first stream comprising aminoethanol hydrogen sulfate ester (AES) and the second stream comprising an aqueous solution of sodium sulfite ($Na_2SO_3$) are each degassed with an inert gas prior to being continuously added to the sulfonation vessel.

19. The process of claim 18, wherein the inert gas is selected from the group consisting of nitrogen, argon, helium, and combinations thereof.

* * * * *